(12) United States Patent
McKinnon

(10) Patent No.: US 6,591,127 B1
(45) Date of Patent: Jul. 8, 2003

(54) INTEGRATED MULTI-MODALITY IMAGING SYSTEM AND METHOD

(75) Inventor: Graeme C. McKinnon, Hartland, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/268,401

(22) Filed: Mar. 15, 1999

(51) Int. Cl.[7] .............................. A61B 5/055; A61B 6/00
(52) U.S. Cl. .......................... 600/411; 600/427; 378/63
(58) Field of Search ................................ 600/407, 411, 600/425, 427, 439, 415; 601/4; 378/62–65; 324/307, 309

(56) References Cited

U.S. PATENT DOCUMENTS

| | | | | |
|---|---|---|---|---|
| 4,543,959 A | * | 10/1985 | Sepponen | 600/411 |
| 5,165,410 A | * | 11/1992 | Warne et al. | 600/436 |
| 5,271,400 A | | 12/1993 | Dumoulin et al. | 128/653.2 |
| 5,526,814 A | * | 6/1996 | Cline et al. | 601/3 |
| 5,553,618 A | * | 9/1996 | Suzuki et al. | 600/407 |
| 5,590,653 A | * | 1/1997 | Aida et al. | 600/411 |
| 5,662,109 A | * | 9/1997 | Hutson | 600/407 |
| 5,672,877 A | * | 9/1997 | Liebig et al. | 250/363.04 |
| 5,740,802 A | * | 4/1998 | Nafis et al. | 600/407 |
| 5,779,637 A | * | 7/1998 | Palkovich et al. | 600/415 |
| 5,818,901 A | * | 10/1998 | Schulz | 378/63 |
| 5,897,495 A | * | 4/1999 | Aida et al. | 600/411 |
| 5,995,108 A | * | 11/1999 | Isobe et al. | 345/421 |
| 6,011,396 A | * | 1/2000 | Eckels et al. | 600/415 |
| 6,031,888 A | * | 2/2000 | Ivan et al. | 378/20 |
| 6,198,957 B1 | * | 3/2001 | Green | 600/411 |
| 6,263,043 B1 | * | 7/2001 | Maschke | 378/63 |
| 6,385,481 B2 | * | 5/2002 | Nose et al. | 600/415 |

FOREIGN PATENT DOCUMENTS

EP    0 673 621 A1    9/1995    ............ A61B/5/00

* cited by examiner

*Primary Examiner*—Ruth S. Smith
(74) *Attorney, Agent, or Firm*—Fletcher, Yoder & Van Someren

(57) ABSTRACT

An integrated, multi-modality imaging technique is disclosed. The embodiment described combines a split-magnet MRI system with a digital x-ray system. The two systems are employed together to generate images of a subject in accordance with their individual physics and imaging characteristics. The images may be displaced in real time, such as during a surgical intervention. The images may be registered with one another and combined to form a composite image in which tissues or objects difficult to image in one modality are visible. By appropriately selecting the position of an x-ray source and detector, and by programming a desired corresponding slice for MRI imaging, useful combined images may be obtained and displayed.

21 Claims, 3 Drawing Sheets

INTEGRATED MULTI-MODALITY IMAGING SYSTEM AND METHOD

FIELD OF THE INVENTION

The present invention relates generally to the field of imaging systems such as those used in medical diagnostics. More particularly, the invention relates to an integrated system that makes use of different modalities in a complementary fashion to permit feedback to surgeons and other medical professionals of physical conditions of a subject, particularly during interventionary procedures.

BACKGROUND OF THE INVENTION

A wide variety of imaging systems have been developed and are presently in use in the medical field. The systems may be generally categorized in a series of "modalities," with each modality being characterized by its particular physics, control, utility, and so forth. For example, magnetic resonance imaging (MRI) systems are commonly employed for producing images of gyromagnetic material within a subject of interest. Over recent years, such systems have become particularly refined in producing high quality and reliable images of internal organs and other particular types of tissue, in various orientations within the subject. X-ray-based techniques have also grown considerably from their initial roots in analog systems utilizing photographic film. Modern x-ray-based modalities include digital x-ray systems which produce electronic data sets representative of picture elements or pixels within an array that can be reconstructed into a useful and high quality image. Other x-ray-based techniques include computed tomography (CT) systems in which x-ray radiation traverses a subject, impacts a detector, and resulting signals are reconstructed by a computer into a useful image through the subject. Still other modalities include positron emission tomography (PET), ultrasound, and so forth.

While the various modalities of imaging systems used in the medical field have improved dramatically in recent years, and continue to improve, they have tended to develop in isolation. MRI systems, for example, are typically used for specific purposes, such as imaging soft tissues. X-ray-based modalities are often used in other situations for which MRI systems are less suitable. In such systems, where images are desired of tissues or anatomies which cannot normally be identified or contrasted from neighboring structures, various approaches may be employed to provide the desired contrast, typically through the use of liquid contrast agents which are injected into the patient prior to the examination sequence. These contrast agents, however, do not necessarily provide the particular tissue identification desired, may not be retained for the time and in the locations desired for the entire procedure, and may cause complications for certain patients. Other techniques have been developed to attempt to identify probes, catheters, and the like, through the use of one or another modality system. Such probes, for example, may include coils which respond to the pulse sequences of MRI systems, to provide feedback to a surgeon during a surgical intervention such as catheterization, and so forth.

In certain procedures, it would be useful to provide additional feedback to medical personnel of the state of tissues and anatomies based upon a combination of imaging modalities. For example, during catheterization, angioplasty, and similar procedures, MRI systems may permit a surgeon to identify soft tissues through which a probe is inserted, but are not necessarily well suited to imaging tissues indicative of the actual location of the probe. Because surgical interventions happen in real time, currently available technologies for separate modality imaging are simply ill suited to providing this type of information and feedback. There is a need, therefore, for an improved technique for supplying anatomical images to medical professionals which overcomes the limitations of separate modalities such as MRI and x-ray-based systems.

SUMMARY OF THE INVENTION

The present invention provides an integrated imaging system designed to respond to these needs. The technique may be applied as a combination of various different imaging modalities, but is particularly well suited to combining MRI systems with x-ray-based systems, such as digital x-ray fluoroscopy systems. The systems are combined in a complimentary and cooperative manner, such that real-time images may be produced of soft tissues through use of MRI imaging sequences, while images of more dense or contrasting tissues and objects may be produced through the x-ray system. The systems may be physically combined by positioning a specially-adapted support structure for a digital x-ray apparatus in an MRI system. Separate images may be produced by the two systems, with the desired anatomy of soft tissues being projected on a screen associated with the MRI system, while the x-ray image is displayed on a separate screen. Alternatively, the system may be adapted to register and combine the images to provide real-time feedback of all of the structures of interest, thereby making use of the strength of the combined modalities in the resulting imaging. In addition to real-time imaging, the system may be employed to produce images which are registered or associated with one another, with the still images being available for viewing, storage, transmission, and so forth.

DETAILED DESCRIPTION OF THE INVENTION

Figure 1:
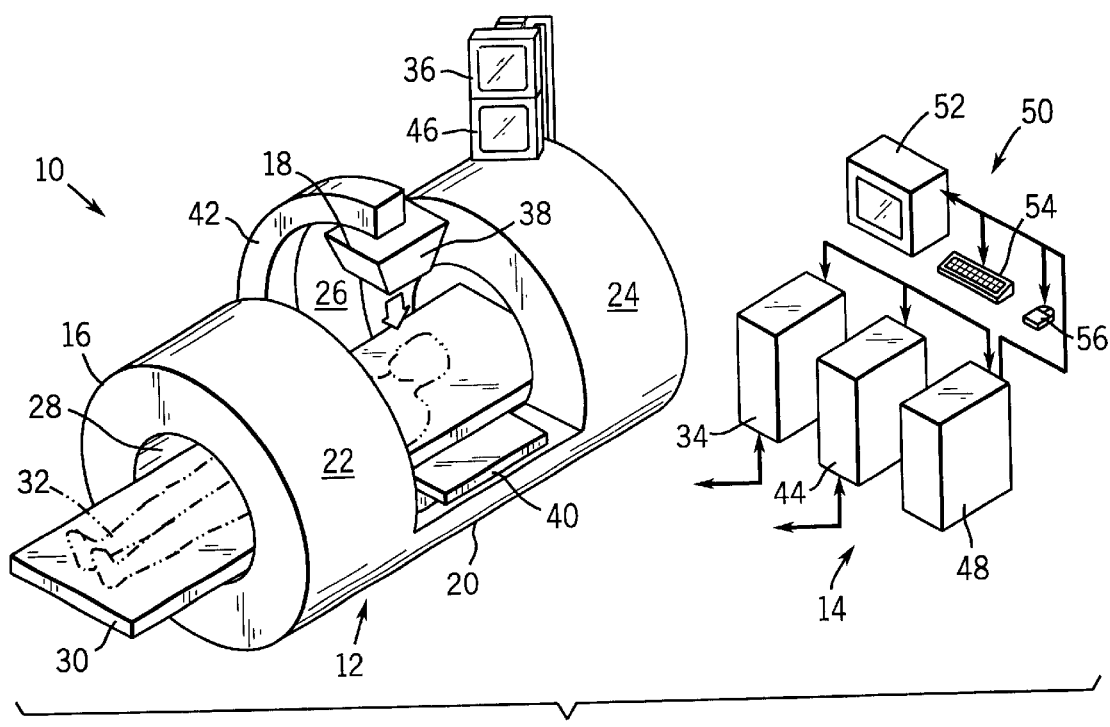
FIG. 1 is a diagrammatical representation of an integrated, multi-modality imaging system for use in producing images of internal tissues of a patient in a medical procedure.

Turning now to the drawings, and referring first to FIG. 1, an integrated, multi-modality imaging system 10 is illustrated as including a data acquisition station 12 and a data processing and control station 14. In the illustrated embodiment, the imaging system includes components of magnetic resonance imaging (MRI) and x-ray modalities. Specifically, the system includes a split magnet MRI system 16 and a digital x-ray system 18 configured to generate images during a medical procedure to provide feedback to a medical diagnostic or surgical team. It should be noted, however, that while the MRI and x-ray modalities described herein are combined by way of example, various other modalities may be combined in similar manners to draw upon the strengths of the particular imaging modalities involved in viewing specific tissues, surgical devices, anatomical features and physiological functions.

In the arrangement illustrated in FIG. 1, MRI system 16 includes a coil housing 20 which is divided into a left-hand section 22 and a right-hand section 24 separated by an opening or access region 26. Generally perpendicular to opening 26, housing 20 forms a patient aperture 28 designed to receive a table 30 on which a patient 32 may be positioned. The patient may thus be disposed at various locations within the coil housing to orient desired portions of the patient's anatomy within the region of opening 26 and to extend regions of the patients anatomy beyond an end of the housing, such as for access to the patient's legs or abdomen. MRI system 16 further includes an MRI controller, designated generally by reference numeral 34 in FIG. 1 and a viewing screen 36 positioned adjacent to the data acquisition station for displaying reconstructed images based upon the magnetic resonance imaged data acquired via the scanner.

X-ray system 18 includes an x-ray source 38 positionable within or adjacent to opening 26 on one side of the patient, and a digital detector array 40 positionable on an opposite side of the patient. The x-ray source and digital detector may be movable together on a fully or partially rotatable gantry 42, such as for selecting an appropriate imaging orientation with respect to the patient. X-ray system 18 further includes an x-ray system controller 44 for regulating operation of the x-ray source and detector, and for collecting and processing image data during operation. An x-ray image viewing screen 46 is provided adjacent to the data acquisition station 12 for displaying x-ray images to the medical diagnostic or surgical team.

An integrated system controller 48 is linked to MRI controller 34 and to x-ray system controller 44 to coordinate production of the desired images, as well as to perform combinations or composites of multi-modality images as described more fully below. Data processing and control station 14 further includes components for facilitating interfacing with a radiologist, clinician, or a member of a surgical team, as indicated generally at reference numeral 50. Thus, operation station 50 may include such peripheral devices as a computer monitor 52, and input devices such as a standard computer keyboard 54 and mouse 56. In addition to the components illustrated diagramatically in FIG. 1, the system may further include communications components for transmitting images generated by the data acquisition station to remote locations, such as for teleradiology techniques, and for storing or archiving images, such as picture archiving and communication systems.

Figure 2:
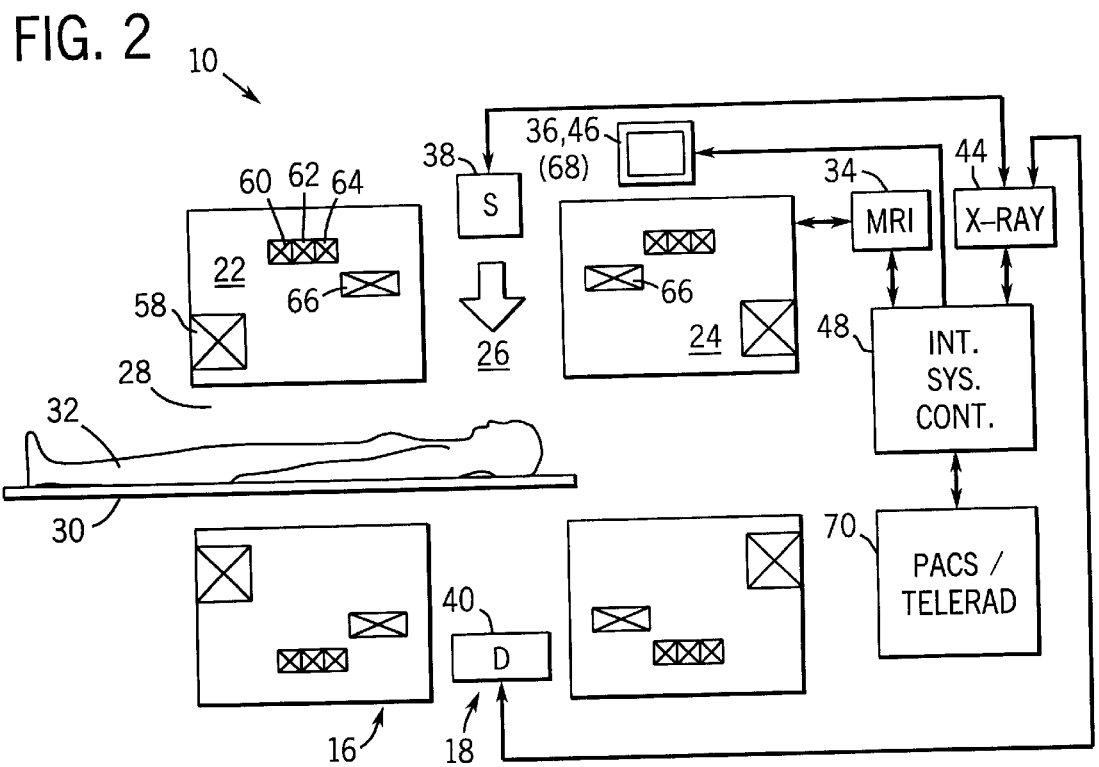
FIG. 2 is a block diagram representing the principle structures of the systems of the embodiment of FIG. 1.

FIG. 2 represents certain of the operational components of the MRI and x-ray systems in somewhat greater detail. As will be appreciated by those skilled in the art, MRI system 16 includes a series of coils which can be precisely controlled to generate desired magnetic fields and radio frequency pulses to produce and sense magnetic resonance emissions from gyromagnetic material within the patient anatomy. These coils include a primary field coil 58 which generates a uniform magnetic field generally aligned with patient bore 28. Gradient field coils 60, 62 and 64 are provided for generating magnetic gradient fields generally orthogonally oriented with respect to one another. A radio frequency coil 66 is provided for generating pulsed radio frequency signals in response to which the gyromagnetic material will produce the magnetic resonance emissions. In particular, the coils of system 16 are controlled by external circuitry to generate desired fields and pulses, and to read emissions from the gyromagnetic material in a controlled manner.

As will be appreciated by those skilled in the art, when the material, typically bound in tissues of the patient, is subjected to the primary field, individual magnetic moments of the paramagnetic nuclei in the tissue attempt to aligned with the field but precess in a random order at their characteristic or Larmor frequency. While a net magnetic moment is produced in the direction of the polarizing field, the randomly oriented components of the moment in a perpendicular plane generally cancel one another. During an examination sequence, an RF frequency pulse is generated at or near the Larmor frequency of the material of interest, resulting in rotation of the net aligned moment to produce a net transverse magnetic moment. Radio signals are emitted following the termination of the excitation signals. This magnetic resonance signal is detected in the scanner and processed for reconstruction of the desired image.

Gradient coils 60, 62 and 64 serve to generate precisely controlled magnetic fields, the strength of which vary over a predefined field of view, typically with positive and negative polarity. When each coil is energized with known electric current, the resulting magnetic field gradient is superimposed over the primary field and produces a linear variation in the overall magnetic field strength across the field of view. Combinations of such fields, orthogonally disposed with respect to one another, enable the creation of a linear gradient in any direction by vector addition of the individual gradient fields.

The gradient fields may be considered to be oriented both in physical planes, as well as in logical axes. In the physical sense, the fields are mutually orthogonally oriented to form a coordinate system which can be rotated by appropriate manipulation of the pulsed current applied to the individual field coils. In a logical sense, the coordinate system defines gradients which are typically referred to as slice select gradients, frequency encoding gradients, and phase encoding gradients.

The slice select gradient determines a slab of tissue or anatomy to be imaged in the patient. The slice select gradient field may thus be applied simultaneous with a selective RF pulse to excite a known volume of spins within a desired slice that precess at the same frequency. The slice thickness is determined by the bandwidth of the RF pulse and the gradient strength across the field of view.

A second logical gradient axis, the frequency encoding gradient axis is also known as the readout gradient axis, and is applied in a direction perpendicular to the slice select gradient. In general, the frequency encoding gradient is applied before and during the formation of the MR echo signal resulting from the RF excitation. Spins of the gyromagnetic material under the influence of this gradient are frequency encoded according to their spatial position across the gradient field. By Fourier transformation, acquired signals may be analyzed to identify their location in the selected slice by virtue of the frequency encoding.

Finally, the phase encode gradient is generally applied in a sequence before the readout gradient and after the slice select gradient. Localization of spins in the gyromagnetic material in the phase encode direction is accomplished by sequentially inducing variations in phase of the precessing protons of the material by using slightly different gradient amplitudes that are sequentially applied during the data acquisition sequence. Phase variations are thus linearly imposed across the field of view and spatial position within the slice is encoded by the polarity and the degree of phase difference accumulated relative to a null position. The phase encode gradient permits phase differences to be created among the spins of the material in accordance with their position in the phase encode direction.

As will be appreciated by those skilled in the art, a great number of variations may be devised for pulse sequences employing the logical axes described above. Moreover, adaptations in the pulse sequences may be made to appropriately orient both the selected slice and the frequency and phase encoding to excite the desired material and to acquire resulting MR signals for processing.

X-ray system 18 provides imaging of anatomies which are less suitable for MRI imaging, including images of bone, external probes, catheters, and so forth. X-ray source 38 will typically include a collimator which permits a stream of radiation to pass into opening 26 in which the patient is positioned. A portion of the radiation passes through and around the subject and impacts digital x-ray detector 40. Detector 40 converts the x-ray photons received on its surface to electrical signals which are acquired and processed to reconstruct an image of the features within the subject patient.

In a presently preferred embodiment, detector 40 consists of a scintillator that converts the x-ray photons received on the detector surface during examinations to lower energy (light) photons. An array of photo detectors then converts the light photons to electrical signals which are representative of the number of photons or intensity of the radiation impacting individual pixel regions of the detector regions. Readout electronics convert the resulting analog signals to digital values that are processed, stored, and displayed as reconstructed images on display screen 36. The array of photo detectors may be made of a single piece of amorphous silicon. The array elements are organized in rows and columns with each element consisting of a photo diode and a thin film transistor. The cathode of each diode is connected to the source of the transistor, and the anodes of all diodes are connected to a negative bias voltage. The gates of the transistors in each row are connected together and the row electrodes are connected to scanning electronics for reading the analog signals produced upon receipt of radiation. The drains of the transistors in a column are connected together and an electrode for each column is connected to readout electronics. The detector permits images to be produced by sequentially enabling rows of a detector and reading out the signals corresponding to the individual picture element or pixel regions.

In the illustrated embodiment, MRI system 16 and x-ray system 18 are coupled to their respective controllers 34 and 44, and their operation is coordinated through integrated system controller 48. System controller 48 may be located in the immediate vicinity of the data acquisition station, typically in or near a surgical ward. The system may transmit images in real time or from memory to PACS and teleradiology stations, as indicated at reference numeral 70 in FIG. 2. Moreover, system controller 48 may combined images generated through the MRI and x-ray modalities, and by other modalities where desired, to utilize the strengths of both modalities. In the embodiment of FIG. 2, such combined images may be displayed on a single viewing screen as indicated at reference numeral 68.

As will be appreciated by those skilled in the art, MRI systems are particularly well suited to imaging certain soft tissues comprising gyromagnetic or paramagnetic molecules. X-ray systems, on the other hand, are particularly well suited to imaging other types of materials having densities or absorption properties which provide contrast when viewed in the x-ray radiation band. By generating both MRI and x-ray images in real time, or in sufficiently closely spaced sequential sampling periods to provide useful feedback to surgical teams, the surgical teams may continuously monitor the location of tissues and interventional tools during a surgical procedure. Moreover, by orienting the source 38 and detector 40 of the x-ray system in a position which is complementary to slices generated by MRI system 16, projections may be generated by integrated system controller 48 which include registered images from both modalities combined to illustrate the position of various tissues or of interventional tools and the like within the imaged tissues.

Figure 3:
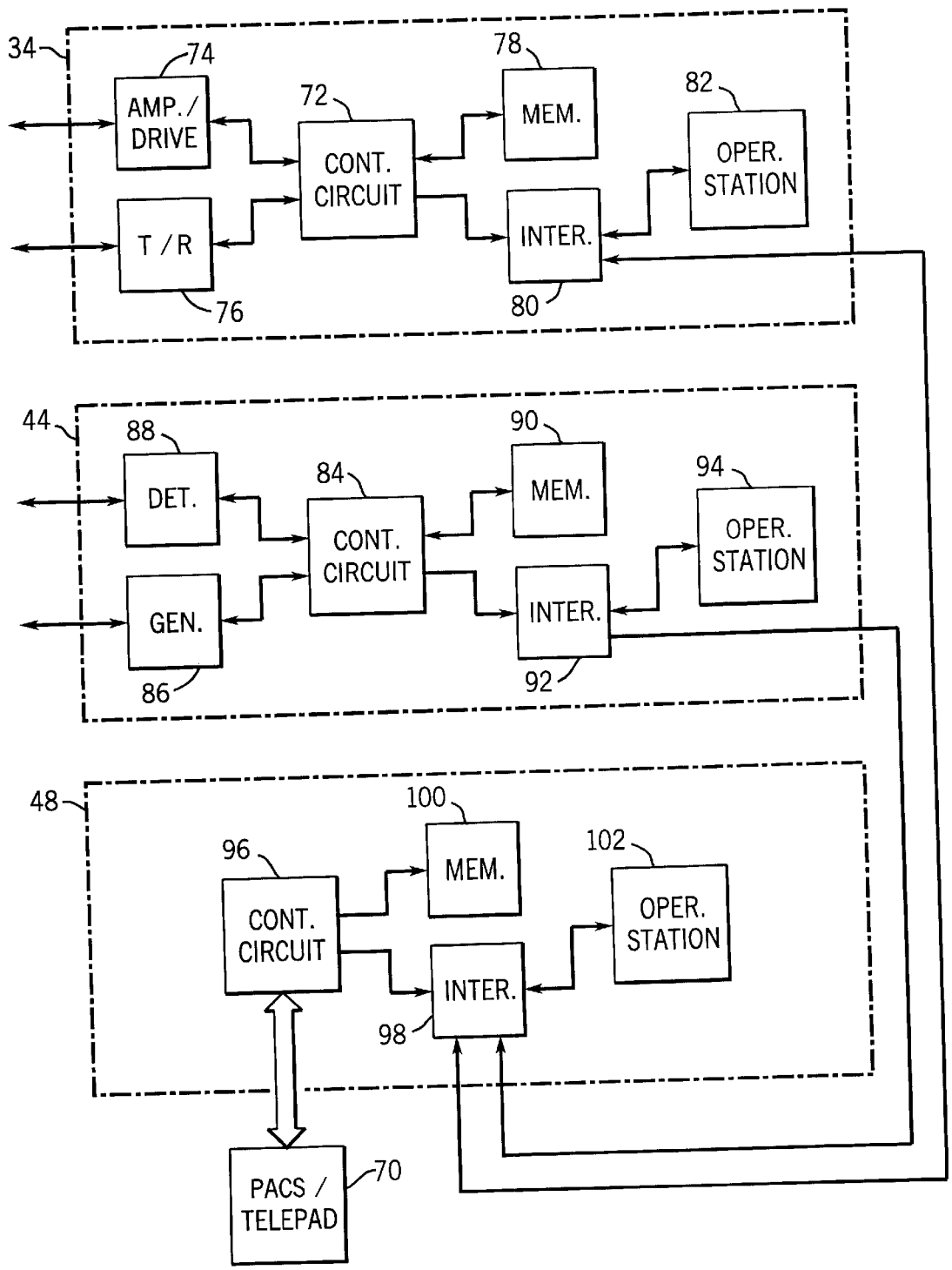
FIG. 3 is a functional block diagram illustrating the various functional subsystems of the arrangement of FIG. 1 and FIG. 2 for use in producing both separate and combined images; and, FIG. 4 and FIG. 5 are exemplary images produced through use of the integrated system in accordance with certain aspects of the present technique, for imaging the location of a probe in a blood vessel of a subject.

Functional circuitry for the control of the MRI and x-ray components of system 10 and for processing resulting image data is represented diagrammatically in FIG. 3. As shown in FIG. 3, MRI controller 34 includes a control circuit 72 which may itself include a central processing unit or digital signal processor of a general purpose or application-specific computer or work station. Control circuit 72 implements programming code for executing specific pulse sequences in the commanded MRI examinations and produces the pulse sequences via amplifier and drive circuitry 74 and transmission and receive circuitry 76. In general, circuitry 74 includes amplification electronics for converting the drive commands for gradient coils 60, 62 and 64 to electrical pulses which generate the desired magnetic fields. Similar command signals are applied by control circuit 72 to circuitry 76 to drive RF coil 66. In the illustrated embodiment, circuitry 76 includes both transmission and receive electronics for amplifying the RF command signals in an active mode, and for receiving resulting magnetic resonance signals in a passive mode. The signals are applied by circuitry 76 to control circuit 72 for processing. Control circuit 72 is also coupled to memory circuitry 78, such as volatile and non-volatile memory, for storing pulse sequence descriptions, examination protocols, configuration parameters, image data, and so forth. Interface circuitry 80 is provided for communicating examination requests, configuration parameters, and image data between MRI controller 34 and integrated system controller 48.

X-ray system controller 44 also includes a control circuit 84 which, similarly, may include a central processing unit or digital signal processor of a conventional computer or work station. Control circuit 84 is coupled to generator circuitry 86 which controls the production of x-ray radiation at source 38. As will be appreciated by those skilled in the art, generator 86 commands electrical discharges within an x-ray tube to produce a stream of x-ray radiation upon onset of an x-ray examination. Control circuit 84 is also coupled to detector interface circuitry 88 which serves to receive and process signals from detector 40. Detector interface circuitry 88 is configured to originate timing and control commands for row and column drivers of the detector and to process resulting signals sampled from the detector. The detector control circuitry 88, and control circuit 84 execute various signal processing and filtration functions, such as for adjustment of dynamic ranges, interleaving of digital image data, and so forth. The circuitry thus commands operation of the x-ray imaging system to execute examination protocols and to process the acquired image data. The examination protocols carried out by the circuitry will be defined in code stored in memory circuit 90. Memory circuit 90 may also serve to store system configuration parameters and image data, both raw and processed. An interface circuit 92 is provided for exchanging such parameter configuration data and image data between control circuit 44 and integrated system controller 48.

Both control circuitry 34 and 44 may include separate operator work stations for regulating their functions independent of integrated system controller 48. In the embodiment illustrated in FIG. 3, therefore, operator stations 82 and 84 are provided in controllers 34 and 44, respectively. Where desired, functionality for operator interface may be combined into one single work station, such as a work station 102 associated with integrated system controller 48.

Integrated system controller 48 includes a control circuit 96 which, again, may comprise a standard central processing unit or digital signal processor of a general purpose or application-specific computer. Code executed by control circuit 96 is stored in memory circuitry 100 which may comprise both volatile and nonvolatile memory, tape drives, optical storage devices, and so forth. Interface circuitry 98 is networked with interface circuitry 80 and 92 of the individual system controllers, to permit the exchange of examination requests and configurations, and the transfer of both raw and processed image data. Operator station 102 permits the surgical team to configure and regulate the operation of controller 48, and to process images acquired during procedures.

Figure 4:
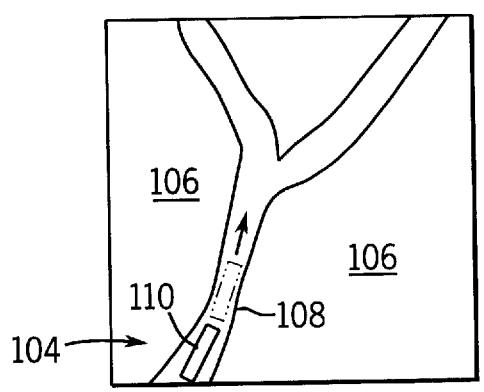
Figure 5:
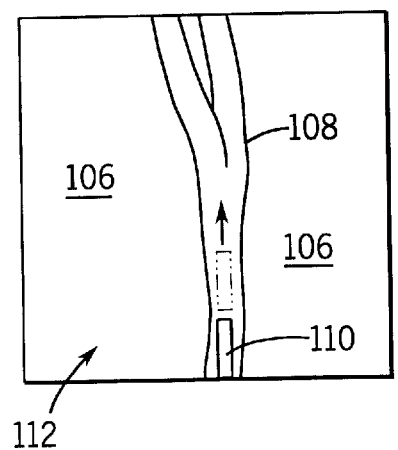

As described above, images produced and processed by MRI and x-ray systems 16 and 18 may be displayed separately or combined to provide registered feedback of various tissues, instruments, or features of interest. FIGS. 4 and 5 represent such registered or combined images produced by both systems. In FIG. 4, an image 104 of tissue 106, and a blood vessel 108, is produced by scaling an overlaying of both MRI and x-ray data. The data may be acquired at any convenient orientation, such as to provide a plan view of the blood vessel as a probe or catheter 110 is advanced during a surgical procedure. As shown in FIG. 5, a similar image 112 may be generated by re-orientation of the source and detector of the x-ray system and by selecting a correspondingly oriented imaging slice for the MRI system, to produce a similar image, but in a different projection to permit a surgical team to follow the advance of the probe 110.

The foregoing technique, combining MRI and fluoroscopy imaging technologies, may be employed in a number of procedures and applications. For example, as illustrated in FIGS. 4 and 5, the technique may be used to image blood vessels and advancing catheters so as to avoid the need for contrast agents employed in conventional procedures. Similarly, the arrangement may be employed in angioplasty procedures, such as to track the deployment or positioning of a stent and to image the degree to which probes, catheters, or stints influence the flow of blood visible via magnetic resonance imaging. The technique may also be applied for application of specific drugs or treatments to specific locations, such as in regions of the brain or for treatment of tumors. In such cases, high atomic weight materials may be employed to absorb x-rays but to avoid generating induced currents which may affect the magnetic resonance images.

Although in the foregoing description, reference has been made to a use of the integrated imaging system in various surgical procedures, it should be noted that the system may be employed for imaging purposes alone. Thus, by combination of different imaging modalities such as MRI and x-ray systems, a patient may be positioned once for creation of separate or composite images via both modalities. Again, the particular image and image orientation may be selected by appropriately positioning the x-ray source and detector, and by selecting a corresponding slice for MRI imaging.

What is claimed is:

1. A medical diagnostic system for providing images of a subject of interest, the system comprising:

a magnetic resonance imaging system having left and right sections separated by an opening, and including a scanner and control circuitry for generating magnetic resonance imaging data of a first portion of the subject disposed within the opening;

an x-ray imaging system including a source of x-ray radiation, a detector and control circuitry for generating x-ray imaging data of the first portion of the subject disposed within the opening;

the magnetic resonance imaging system and the x-ray imaging system cooperating to generate respective imaging data in real time such that reconstructed images of the first portion of the subject based upon the image data can be displayed at the diagnostic system; and an integrated system controller coupled to the magnetic resonance imaging system and to the x-ray imaging system for coordinating operation of the imaging systems for generation of respective imaging data and for reconstructing an image of the first portion of the subject from the magnetic resonance imaging data and the x-ray imaging data.

2. The diagnostic system of claim 1, wherein the x-ray imaging system is adapted to generate the x-ray imaging data of the subject within the opening and in which the x-ray source and detector are movable about the magnetic resonance images scanner.

3. The diagnostic system of claim 1, wherein the magnetic resonance imaging system has a longitudinal axis, the x-ray imaging system includes a source for emitting x-ray radiation and a radiation detector for receiving a portion of the radiation, and wherein x-ray radiation is emitted in a direction generally transverse to the longitudinal axis.

4. The diagnostic system of claim 1, wherein the magnetic resonance imaging system and the x-ray imaging system generate the respective image data at least partially simultaneously.

5. The diagnostic system of claim 1, further comprising at least one display device for reproducing reconstructed images generated from the respective magnetic resonance and x-ray image data.

6. The diagnostic system of claim 5, wherein the images are displayed on separate display devices.

7. The diagnostic system of claim 1, wherein the integrated system controller generates combined images based upon the magnetic resonance image data and the x-ray image data.

8. An integrated, multi-modality medical imaging system comprising:

a split-magnet MRI scanner having left and right sections separated by an opening, the left and right sections each including portions of a primary magnet and gradient coils for generating controlled magnetic gradient fields, a radio frequency coil, an MR signal receiving coil and control circuitry coupled to the scanner for regulating operation of the coils for generation of MR image data, the split-magnet MRI scanner generating MR image data of a portion of a subject situated within the opening between the left and right sections of the MRI scanner;

a digital x-ray imaging station including a source of x-ray radiation and a digital detector, and control circuitry for regulating operation of the source and the detector for generation of x-ray image data, the x-ray imaging station positioned for generating x-ray image data of the portion of a subject situated within the opening between the left and right sections of the MRI scanner and in which the source and detector are movable about the MRI scanner in the opening of the split-magnet MRI scanner; and an integrated system controller for coordinating acquisition of image data via the MRI and x-ray imaging systems.

9. The imaging system of claim 7, further comprising at least one monitor for displaying an image reconstructed based upon at least one of the MRI or the x-ray image data.

10. The imaging system of claim 9, comprising first and second monitors for displaying reconstructed images based upon the MR image data and the x-ray image data, respectively.

11. The imaging system of claim 10, wherein the monitor displays images reconstructed from the MRI image data and the x-ray image data.

12. The imaging system of claim 8, wherein the source and detector of the x-ray imaging system are disposed to generate the x-ray image data in a direction generally transverse to a longitudinal axis of the MRI scanner.

13. An integrated, multi-modality imaging system comprising:

a first system of a first modality configured to generate first image data of a first region of a subject in a first manner;

an x-ray imaging system including a source of x-ray radiation, a detector and control circuitry for generating x-ray imaging data of the subject, wherein a vertical opening in the first system allows access to a target region for the x-ray imaging system and for procedures performed on the target region within the system, wherein the target region is a portion of the first region of the subject; and an integrated system controller coupled to the first system and the x-ray system for coordinating generation of the first and x-ray image data.

14. The imaging system of claim 13, wherein the first modality is a magnetic resonance imaging modality.

15. The imaging system of claim 13, wherein the first image data and the x-ray image data are generated at least partially simultaneously.

16. The imaging system of claim 13, further comprising display means for displaying reconstructed images based upon the image data.

17. A method for producing images of a subject of interest, the method comprising the steps of:

(a) providing an integrated imaging system including a split-magnet MRI system having left and right sections separated by an opening and adapted to provide MRI image data of a subject disposed within the opening, an x-ray system adapted to provide x-ray image data of a subject disposed within the opening, and an integrated system controller operable to control operation of the MRI system and the x-ray system;

(b) coordinating generation of MRI and x-ray image data of a region of interest using the integrated system controller;

(c) generating MRI image data of a portion of a subject disposed within the opening via the MRI system;

(d) generating x-ray image data of the portion of the subject disposed within the opening via the x-ray system;

(e) reconstructing images of the region of interest based upon the MRI image data and the x-ray image data using the integrated system controller, (f) displaying the reconstructed images at the integrated imaging system; and (g) performing a surgical procedure on the portion of the subject disposed within the opening.

18. The method of claim 17, wherein steps (c) and (d) are performed at least partially simultaneously.

19. The method of claim 17, wherein step (e) includes a step of combining the MRI and x-ray image data.

20. The method of claim 17, wherein steps (c) and (d) are repeated for subsequent image data sets while images reconstructed from previous image data sets are displayed.

21. The method of claim 17, comprising the further step of positioning components of the x-ray system to produce a projection image corresponding to an image slice selected via the MRI system.

* * * * *